United States Patent [19]

Lambrecht et al.

[11] 4,252,668

[45] Feb. 24, 1981

[54] PROCESS FOR PREPARATION OF POTASSIUM-38

[75] Inventors: Richard M. Lambrecht, Quogue; Alfred P. Wolf, Setauket, both of N.Y.

[73] Assignee: The United States of America as represented by the United States Department of Energy, Washington, D.C.

[21] Appl. No.: 14,179

[22] Filed: Feb. 22, 1979

[51] Int. Cl.$^3$ .............................................. G21G 1/10
[52] U.S. Cl. ......................... 252/301.1 R; 250/432 R; 250/492 R; 423/2; 423/249
[58] Field of Search .................................. 423/2, 249; 252/301.1 R; 250/432 R, 492 R, 492 B; 176/11, 16

[56] References Cited

PUBLICATIONS

Myers, W. G. "Radiopotassium-38 . . ." *J. Nucl. Med.*, 1973, 14(6) 359-360 as abstracted in Chem. Abs. 79 (1976): 39705g.
Clark et al. "The Production of Potassium-43 . . ." *Int'l. J. Appl. Rad. & Isotopes*, 1972, vol. 23, pp. 329-335.
Chem. Abstracts 66 (1967): 71108q.
Bruge et al. "($^3$He,t) reaction mechanism . . ." *Phys. Rev. C* 19(1), 1979, pp. 9-19.

*Primary Examiner*—Deborah L. Kyle
*Attorney, Agent, or Firm*—James E. Denny; Dean E. Carlson; Leonard Belkin

[57] ABSTRACT

A solution of potassium-38 suitable for use as a radiopharmaceutical and a method for its production. Argon is irradiated with protons having energies above the threshold for the $^{40}$Ar(p,3n)$^{38}$K reaction. The resulting potassium-38 is dissolved in a sterile water and any contaminating chlorine-38 is removed.

12 Claims, No Drawings

PROCESS FOR PREPARATION OF POTASSIUM-38

BACKGROUND OF THE INVENTION

This invention relates to the production of radiopharmaceuticals and more particularly to production of potassium-38.

The invention described herein was made or conceived in the course of, or under a contract with, the United States Department of Energy.

Potassium-38 has ideal physiological and physical characteristics for use as a radiopharmaceutical. Physiologically potassium-38 is preferentially extracted into the heart, while its decay characteristics, 200% abundance of positron annihilation photons ($E_{\beta+}$ = 2.7 MeV) and approximately 100% abundance of 2.17 MeV photons make it highly suitable for positron emission tomography. Further, its halflife of approximately 7.62 minutes allows its use with a relatively low radiation dosage to the patient. This combination of characteristics makes potassium-38 an ideal agent for the quantitative measurement of myocardial perfusion.

While the use of potassium-38 in nuclear medicine has been suggested, and potassium-38 has been produced for nuclear physics experiments, prior to the subject invention there was no known method for its routine production in quantities and form suitable for use as a radiopharmaceutical. Further, methods previously known in nuclear physics did not contemplate the rapid preparation of the product potassium-38 for use as a radiopharmaceutical.

By "suitable for use as a radiopharmaceutical" herein is meant an essentially pure and sterile solution of potassium-38, and its decay products, in water having a total activity, at the time of injection, of from 1 to 10 mCi, in a volume of from 1-5 milliliters.

PRIOR ART

Several reactions for the production of potassium-38 are given in the literature. In particular reactions on Ca and Cl salt targets have been suggested for the production of potassium as a radiopharmaceutical. However, methods based on these reactions have at least two inherent disadvantages which are overcome by the subject invention. First, as the target compounds are solids excessively long times are required for chemical separation and preparation of the potassium-38 as a radiopharmaceutical. Second, methods based on the above discussed reactions require even more extensive chemical processing to avoid Ca and Cl contamination of the resulting radiopharmaceutical. These problems are substantially overcome by the method of the subject invention.

BRIEF SUMMARY OF THE INVENTION

The subject invention overcomes the above discussed problems by means of a method comprising the steps of first irradiating a target volume of essentially pure argon gas which substantially comprises argon-40 with protons having energies above the threshold for the $^{40}Ar(p,3n)^{38}K$ reaction, rinsing the chamber containing the target gas with sterile water, passing the rinse water through an ion exchange resin so as to remove chlorine-38 produced by the $^{40}Ar(p,2pn)^{38}Cl$ or equivalent reaction, then filtering the rinse water so as to remove any bacteria which may have been introduced, whereby a solution of potassium-38 suitable for use as a radiopharmaceutical is produced.

BRIEF DESCRIPTION OF THE PREFERRED EMBODIMENT

Research grade argon is contained under pressure in a target chamber, having a cooling means associated therewith. Nickel is a preferred material for such target chambers, having proven suitable for the rapid removal of potassium-38 in solution. A preferred target is described as a "Mark I" target by Lambrecht, Neirinckx and Wolf in the *International Journal of Applied Radioactive Isotopes* #29, pg, 175 (1978), which article is hereby incorporated by reference. However, it is to be understood that the details of the target vessel design are not limitive of the subject invention and are given by way of illustration only. Other suitable types of target vessels would be known to those skilled in the art. The argon is then irradiated by energetic protons such as are routinely produced by cyclotrons, having energies above the threshold for the $^{40}Ar(p,3n)^{38}K$ reaction. Preferably energy of about 32.5 MeV degraded to about 29.8 MeV in the target gas is used. This energy range is suitable for the production of potassium-" while minimizing the relative amount of chlorine-" produced. Irradiation is continued until a substantial portion of the saturation level is reached.

By saturation herein is meant the amount of product isotope (i.e. potassium-38) where, for a given set of irradiation conditions, the rate of production equals the rate at which the product isotope is lost by radioactive decay. The irradiation conditions (proton fluence and target gas pressure) and the fraction of saturation to be obtained are chosen so that a sufficient yield for radiopharmaceutical uses can be obtained in a reasonable time, at a reasonable cost. Methods for calculating such conditions are well known to those skilled in the art of radiopharmaceutical production and need not be discussed further here. Satisfactory results have been obtained when a target vessel of 37 ml volume, filled with argon at a pressure of about 6.8 atmo. was irradiated at a fluence of approximately 8 $\mu$A to about 85% of saturation.

After irradiation the target vessel is rinsed with sterile water. Introduction of about 5 ml of water has proven satisfactory to remove 95% of the radiochemical yield in about 3 ml of solution in a single rinse under the above discussed conditions.

The resulting solution is then passed through an ion exchange resin to remove chlorine-38 which is produced by the $^{40}Ar(p,2pn)^{38}Cl$ reaction. A suitable resin is Dowex 1-X8, Cl form, 50-100 mesh, available from the Bio-Rad Laboratories. From the ion exchange resin the solution is passed through a sterile filter suitable to remove any bacteria which may have gotten into the solution and into a sterile syringe for injection.

Under the above discussed conditions potassium-38 is obtained with greater than 99.9% radionuclidic purity with yields of 4.4±0.9 millicuries/ $\mu$Ah. Total time required from the end of irradiation for additional processing is typically 120 sec. Thus, the subject invention provides a method for the rapid (with respect to the potassium-38 half-life of approximately 7.62 min) production of a solution of potassium-38 suitable for radiopharmaceutical use.

EXPERIMENTAL EXAMPLE 1

The nickel target was filled with 100 psig (6.8 atm) of argon which was sufficient to degrade the proton beam from 32 to 29.8 MeV in the gas target. A 0.010" aluminum window was cooled with water flowing at 3 L min$^{-1}$ through the block. The target was irradiated for 30 min at a average beam current of 8 $\mu$A to an integrated dose of 4.0 $\mu$Ah. Following the irradiation the argon was vented by opening a valve. 5 mL of sterile water for injection was then introduced into the target chamber through the open valve by use of a syringe. The target was rigorously rotated for ~5 sec to wet all the walls. and then permitted to drain to the bottom of the target chamber for 18 10 sec. The aluminum window of the target was punctured with a 5 mL pipette equipped with a suction device. The $^{38}$K was withdrawn and purified of $^{38}$Cl by placement of the solution onto a column (120 mm×4 mm i.d.) containing Dowex 1-X8, Cl form, 50–100 mesh. The solution was displaced with a piston through the column and a sterile millipore filter, and into a sterile syringe equipped with a 26 g needle.

The solution was assayed 3 min after the end of the proton bombardment (EOB), and found to contain 14.9 mCi of $^{38}$K. The production rate corrected to EOB was 4.9 mCi/$\mu$Ah.

EXPERIMENTAL EXAMPLE 2

The experimental conditions were idential except the irradiation period was 26 min at an average beam current of 7.9 $\mu$A to give an integrated dose of 3.436 $\mu$Ah. The $^{38}$K produced was assayed as 11.5 mCi at EOB+2.5 min, i.e. resulting in a production rate of 4.2 mCi/$\mu$Ah at EOB.

Variations within the scope of the subject invention on the product and methods disclosed above will be obvious to those skilled in the art. Accordingly, the scope of the invention is defined only by the following claims.

We claim:

1. A method for producing a solution of potassium-38 comprising:
    (a) irradiating a target volume of essentially pure argon gas, said gas substantially comprising argon-40, with protons having energies above the threshold for the $^{40}$Ar(p,3n)$^{38}$K reaction;
    (b) rinsing the chamber containing said gas with sterile water, so as to form a solution of potassium-38;
    (c) treating said solution so as to remove any chlorine-38.

2. The method of claim 1, wherein said protons have energies of about 32.5 MeV.

3. The method of claim 1 wherein said protons have energies substantially above the $^{40}$Ar(p,3n)$^{38}$K threshold and said gas is at a pressure sufficient to degrade said proton energies to about said threshold within said volume.

4. The method of claim 3 wherein said protons enter said target gas with energies of about 32.5 MeV and said energies are degraded to about 29.8 MeV within said volume.

5. The method of claim 4 wherein step (c) is carried out by passing said solution through an ion exchange resin.

6. The method of claim 5, wherein said solution is resterilized.

7. The method of claim 1 wherein said solution is resterilized. after step (c).

8. The method of claim 4 wherein said resterilization is carried out by filtration.

9. The method of claim 1 wherein step (c) is carried out by passing said solution through an ion exchange resin.

10. The method of claim 1 wherein said chamber is formed of nickel.

11. A solution of potassium-38 suitable for use as a radiophrmaceutical made by the method of claims 1, 2, 3, 4, 5, 6, 7, 8, 9, or 10.

12. A sterile solution consisting essentially of potassium-38, its decay products and water, said solution having radioactive purity greater than 99.9% and a total activity and specific activity per milliliter such as to be suitable for use as a radiopharmaceutical.

* * * * *